US010004260B2

(12) United States Patent
Liu

(10) Patent No.: US 10,004,260 B2
(45) Date of Patent: Jun. 26, 2018

(54) ELECTRONIC CIGARETTE

(71) Applicant: Qiuming Liu, Guangdong (CN)

(72) Inventor: Qiuming Liu, Guangdong (CN)

(73) Assignee: HUIZHOU KIMREE TECHNOLOGY CO., LTD. SHENZHEN BRANCH, Shenzhen, Guangdong (CN)

( * ) Notice: Subject to any disclaimer, the term of this patent is extended or adjusted under 35 U.S.C. 154(b) by 1 day.

(21) Appl. No.: 14/360,736

(22) PCT Filed: Feb. 20, 2014

(86) PCT No.: PCT/CN2014/072317
§ 371 (c)(1),
(2) Date: May 27, 2014

(87) PCT Pub. No.: WO2015/120639
PCT Pub. Date: Aug. 20, 2015

(65) Prior Publication Data

US 2016/0366935 A1 Dec. 22, 2016

(30) Foreign Application Priority Data

Feb. 12, 2014 (CN) .................... 2014 2 0063699 U

(51) Int. Cl.
*A24F 47/00* (2006.01)
*A61M 15/06* (2006.01)
(Continued)

(52) U.S. Cl.
CPC ......... *A24F 47/008* (2013.01); *H05B 1/0244* (2013.01); *B65D 23/08* (2013.01); *B65D 2203/04* (2013.01); *H05B 2203/021* (2013.01)

(58) Field of Classification Search
CPC ................................ A24F 47/00; A61M 15/06
See application file for complete search history.

(56) References Cited

U.S. PATENT DOCUMENTS 3,200,819 A * 8/1965 Gilbert .................. A24F 47/008
128/202.21
2009/0230117 A1* 9/2009 Fernando ............. A24F 47/008
219/490
(Continued)

FOREIGN PATENT DOCUMENTS

CN 201753610 U 3/2011
CN 102423145 A 4/2012
(Continued)

OTHER PUBLICATIONS

International Search Report for corresponding application PCT/CN2014/072317; dated Nov. 18, 2014; no english version available until PCT application is published.

*Primary Examiner* — Cynthia Szewczyk
(74) *Attorney, Agent, or Firm* — U.S. Fairsky LLP; Yue Xu

(57) ABSTRACT

An electronic cigarette includes: an atomizing assembly adapted to atomize liquid, a battery rod assembly adapted to supply power to the atomizing assembly, and a liquid storage device adapted to store the liquid; a first screw section and a second screw section are respectively provided at two ends of the atomizing assembly, and a turning direction of the first screw section is opposite to a turning direction of the second screw section. The turning direction of the first screw section is opposite to that of the second screw section. Thus, when the electronic cigarette is under an external screwing force in a certain direction, either the battery rod assembly or the liquid storage device may be unscrewed and taken out, which effectively avoid a mis-operation.

19 Claims, 11 Drawing Sheets

(51) Int. Cl.
*H05B 1/02* (2006.01)
*B65D 23/08* (2006.01)

(56) References Cited

U.S. PATENT DOCUMENTS

| | | | | |
|---|---|---|---|---|
| 2011/0011396 A1* | 1/2011 | Fang | A24F 47/008 128/202.21 |
| 2011/0277761 A1* | 11/2011 | Terry | A24F 47/008 128/203.12 |
| 2012/0174914 A1* | 7/2012 | Pirshafiey | A61M 11/041 128/200.14 |
| 2013/0139833 A1* | 6/2013 | Hon | A24F 47/008 131/273 |
| 2014/0007863 A1* | 1/2014 | Chen | A24F 47/008 128/200.14 |

FOREIGN PATENT DOCUMENTS

| | | | |
|---|---|---|---|
| CN | 202218599 U | 5/2012 | |
| CN | 202603608 U | 12/2012 | |
| CN | 202890464 U | 4/2013 | |
| CN | 202900920 U | 4/2013 | |
| CN | 203015837 U | 6/2013 | |
| CN | 203087526 U | 7/2013 | |
| CN | 203388268 U | 1/2014 | |
| WO | WO 2012152053 A1 * | 11/2012 | A24F 47/008 |

* cited by examiner

ELECTRONIC CIGARETTE

The present application is a National Stage application of PCT international application PCT/CN 2014/072317, filed on Feb. 20, 2014 which claims the priority to Chinese Patent Application No. 201420063699.1 titled "ELECTRONIC CIGARETTE", filed with the Chinese State Intellectual Property Office on Feb. 12, 2014, both of which are incorporated herein by reference in their entireties.

FIELD

The present application relates to the technical field of electronic cigarette, and particularly to an electronic cigarette for preventing a mis-operation.

BACKGROUND

A conventional electronic cigarette includes an atomizing assembly, a liquid storage device and a battery rod assembly. The liquid storage device and the battery rod assembly are arranged at two ends of the atomizing assembly, and are connected with the atomizing assembly in a removable manner through threads. The threads at the two ends of the atomizing assembly have the same turning direction.

The atomizing assembly is connected with both the liquid storage device and battery rod assembly through threads, and the threads at the two end portions of the atomizing assembly are in the same turning direction. When the battery rod assembly is to be taken out for charge, one hand of a user usually holds the liquid storage device and the other hand unscrews the battery rod assembly. At this time, if the liquid storage device is not connected tightly enough with the atomizing assembly and the atomizing assembly is tightly connected with the battery rod assembly, it may happen that the liquid storage device has already been loosely unscrewed from the atomizing assembly, while the battery rod assembly has not yet been unscrewed and taken out. Similarly, when liquid storage device is to be replaced, it may happen that the liquid storage device has not yet been unscrewed, while the battery rod assembly has already been unscrewed.

SUMMARY

In view of this, an electronic cigarette is provided for preventing a mis-operation according to the disclosure.

An electronic cigarette, including:

an atomizing assembly adapted to atomize liquid, a battery rod assembly adapted to supply power to the atomizing assembly, and a liquid storage device adapted to store the liquid; wherein a first screw section and a second screw section are respectively provided at two ends of the atomizing assembly, and a turning direction of the first screw section is opposite to a turning direction of the second screw section;

a fume suction end and a third screw section matched with the first screw section are respectively provided at two ends of the battery rod assembly; and a fourth screw section matched with the second screw section is provided at an open end of the liquid storage device.

In the electronic cigarette, each of the screw sections is a thread section or a swivel coupler section.

In the electronic cigarette, the atomizing assembly and the battery rod assembly are coaxially arranged.

In the electronic cigarette, the atomizing assembly includes:

an electric heating wire assembly adapted to atomize the liquid; and a liquid conveyor adapted to convey the liquid in the liquid storage device to the electric heating wire assembly for atomization.

In the electronic cigarette, the atomizing assembly also includes:

an atomizer holder;

an atomizer electrode fixed inside the first screw section and electronically connected to the electric heating wire assembly;

an insulating ring provided between the first screw section and the atomizer electrode; and an atomizing sleeve provided on the atomizer holder, wherein the liquid conveyer is provided inside the atomizing sleeve.

In the electronic cigarette, multiple liquid conveying holes are provided on a side wall of the atomizing sleeve; and a liquid storage cotton column is provided at an inner side of the liquid conveying holes and adapted to convey the liquid inside the liquid storage device to the atomizing sleeve.

In the electronic cigarette, the battery rod assembly includes:

a battery sleeve;

a battery contained in the battery sleeve;

a battery holder provided in the battery sleeve and adapted to fix the battery; and a battery electrode provided at an end of the battery holder and electronically connected with the battery and the atomizer electrode.

In the electronic cigarette, a suction nozzle, provided as the fume suction end, is connected with the battery sleeve in a removable manner.

In the electronic cigarette, the liquid storage device is a transparent container with scales.

In the electronic cigarette, a sealing ring is provided at a joint of the first screw section of the atomizing assembly and the third screw section of the battery rod assembly.

In the electronic cigarette, the liquid storage device is a glass bottle with scales.

In the electronic cigarette, a fume passage adapted to communicate the fume suction end with an air intake is provided inside the battery rod assembly;

the air intake is provided on a contact surface of the atomizing assembly and the liquid storage device;

or, the air intake is provided on an outer wall of the atomizing assembly.

In the electronic cigarette, a sealing ring adapted to seal the liquid storage device is provided at a joint of the atomizer holder and the liquid storage device.

In the electronic cigarette, an annular sealing plug with a through hole is sealingly engaged with the open end of the liquid storage device; and a pierceable film is provided inside a liquid conveying hole of the annular sealing plug and adapted to seal the through hole.

The electronic cigarette provided according to the disclosure includes: an atomizing assembly adapted to atomize liquid, a battery rod assembly adapted to supply power to the atomizing assembly, and a liquid storage device adapted to store the liquid, where a first screw section and a second screw section are respectively provided at two ends of the atomizing assembly, and a turning direction of the first screw section is opposite to a turning direction of the second screw section, a fume suction end and a third screw section matched with the first screw section are respectively provided at two ends of the battery rod assembly, and a fourth screw section matched with the second screw section is provided at an open end of the liquid storage device. In this embodiment, the turning direction of the first screw section is opposite to the turning direction of the second screw section. Thus, when the electronic cigarette is under an external twisting force in a certain direction, either the battery rod assembly or the liquid storage device may be unscrewed and taken out, which effectively avoids a misoperation.

BRIEF DESCRIPTION OF THE DRAWINGS

In order to more clearly illustrate the embodiments in the disclosure or the technical solution in the prior art, drawings referred to describe the embodiments or the prior art will be briefly described hereinafter. Apparently, the drawings in the following description are only several embodiments of the present application, and for those skilled in the art, other drawings may be obtained based on these drawings without any creative work.

DETAILED DESCRIPTION OF EMBODIMENTS

An electronic cigarette is provided according to the disclosure, a structure of which is illustrated in detail in conjunction with FIG. 1 as follows.

Figure 1:
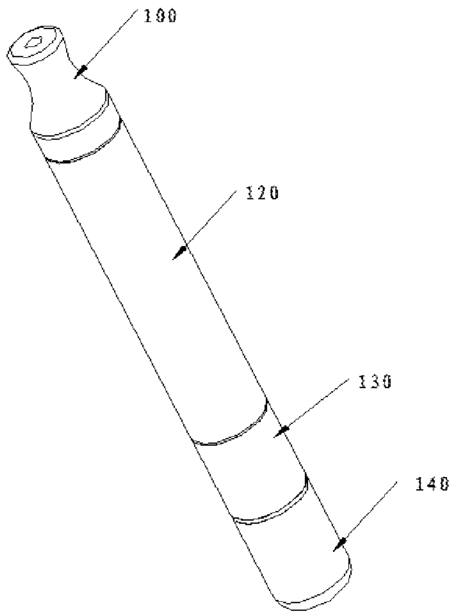
FIG. 1 is an overall structural view of an electronic cigarette according to a preferable embodiment of the disclosure.

As shown in FIG. 1, the electronic cigarette includes: a body of the electronic cigarette.

The body of the electronic cigarette includes: a fume suction end 100, through which a user may such fumes;

A liquid storage device 140 is adapted to store liquid. Specially, atomizable liquid is stored in the liquid storage device 140.

An atomizing assembly 130 is adapted to atomize the liquid. Specially, the liquid in the liquid storage device 140 may be atomized by the atomizing assembly 130.

A liquid and fume passage (not indicated in FIG. 1, please refer to FIG. 6) is adapted to flow the atomized liquid is also formed inside the electronic cigarette. Thus, the user may suck, by the fume suction end 100, the liquid passing through the fume passage.

The electronic cigarette also includes a battery rod assembly 120 adapted to supply power to the atomizing assembly 130.

The atomizing assembly 130 of the electronic cigarette is arranged between the battery rod assembly 120 and the liquid storage device 140.

Preferably, the liquid storage device 140 is connected to the atomizing assembly 130 in a removable manner.

The atomizing assembly 130 is connected to the battery rod assembly 120 in a removable manner.

The advantage of a removable connection manner lies in that, it is convenient for the user to replace the atomizing assembly 130 or remove the liquid storage device 140 whenever necessary, and further it is convenient for the user to add the liquid into the liquid storage device 140 or replace the liquid storage device 140.

The liquid storage device 202 may be connected to the atomizing assembly 203 in an irremovable manner, and/or the atomizing assembly 203 may be connected to the battery rod assembly 204 in an irremovable manner, which will not be limited herein.

In order to achieve a removable connection between the atomizing assembly 130 and the liquid storage device 140, a first screw section and a second screw section are respectively provided at two ends of the atomizing assembly 130, and a turning direction of the first screw section is opposite to a turning direction of the second screw section.

A fume suction end 100 and a third screw section matched with the first screw section are respectively provided at two ends of the battery rod assembly 120. That is, the battery rod assembly 120 may be connected with the atomizing assembly 130 in a removable manner by swiveling and connecting the first screw section and the third screw section.

A fourth screw section matched with the second screw section is provided at an open end of the liquid storage device 140. Thus, the atomizing assembly 130 may be connected with the liquid storage device 140 in a removable manner.

In this embodiment, the turning direction of the first screw section is opposite to that of the second screw section. Thus, when a twisting force in one direction is exerted upon the electronic cigarette, one of the battery rod assembly 120 and the liquid storage device 140 may be removed from the atomizing assembly 130, and if the other one needs to be removed, a twisting force in an opposite direction needs to be exerted upon the electronic cigarette. Therefore, a misoperation may be avoided during the removing process, and the removing efficiency may be effectively improved.

Further referring to FIG. 1, the liquid storage device 140 is provided at an end of the body of the electronic cigarette away from the fume suction end. The advantage of this arrangement manner lies in that, since the liquid storage device 140 is positioned away from the fume suction end 100, a fume passage inside the body of the electronic cigarette does not pass through the liquid storage device 140, therefore un-atomized liquid in the liquid storage device 140 may not be leaked out to the fume passage, and the user may not sucked the un-atomized liquid, which effectively avoids leakage of liquid. Besides, the fume passage, which does not pass through the liquid storage device 140, may also avoid a condensation of fumes in the fume passage, and therefore effectively avoids a block of the fume passage by the condensed liquid.

In this embodiment, the atomizing assembly 130 is positioned between the battery rod assembly 120 and the liquid storage device 140. That is, the atomizing assembly 130 is positioned away from the fume suction end 100. In a case the electronic cigarette provided in this embodiment is smoked by a user, the atomizing assembly 130 is positioned away from the mouth of the user, and thus the heat, generated by atomizing the liquid by the atomizing assembly 130, will not scald the user, which effectively improves the security of the electronic cigarette. Also, in the smoking process, the user may hold the battery rod assembly 120, instead of the exothermic atomizing assembly 130. Thus, in a case the electronic cigarette provided in this embodiment is smoked by the user, his or her hand may not be burnt, and thus the temperature of a real cigarette is effectively imitated, and user experience is improved in the smoking process.

Figure 2:
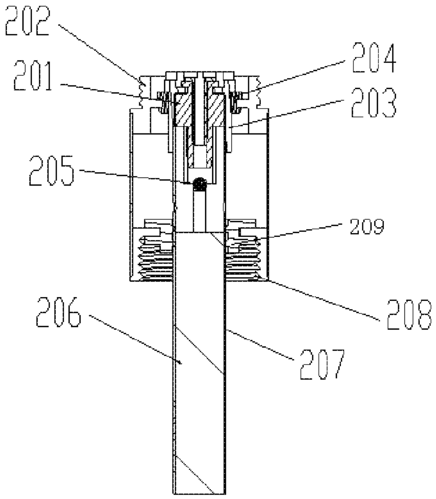
FIG. 2 is a sectional structural view of an atomizing assembly of an electronic cigarette according to another preferable embodiment of the disclosure.

The structure of the electronic cigarette according to the embodiment is illustrated, referring to FIG. 1. The structure of the atomizing assembly of the electronic cigarette is illustrated in conjunction with the embodiment shown in FIG. 2 as follows:

As shown in FIG. 2, the atomizing assembly includes: an atomizer holder 201; a first screw section 202; an atomizer electrode 203; an insulating ring 204; an electric heating wire assembly 205; a liquid conveyer 206; an atomizer sleeve 207; and a second screw section 208.

The first screw section 202 is provided at the top of the atomizer holder 201 and adapted to connect with the battery rod assembly 120 in a removable manner.

The atomizer electrode 203 is fixed inside the first screw section 202.

The insulating ring 204 is provided between the first screw section 202 and the atomizer electrode 203.

The electric heating wire assembly 205 is electronically connected with the atomizer electrode 203 to atomizing the liquid.

The liquid conveyer 206 is adapted to convey the liquid in the liquid storage device 140 to the electric heating wire assembly 205 for atomization. The liquid conveyer specifically may be made of liquid storage cotton or liquid storage fiber, etc., which shall not be limited herein.

The atomizer sleeve 207 is provided on the atomizer holder 201, and the liquid conveyer 206 is provided inside the atomizer sleeve 207.

Specifically, the atomizer sleeve 207 is inserted inside the liquid storage device 140, and at least one liquid conveying hole 301 (shown in FIG. 3) is provided on a surrounding wall of the atomizer sleeve 207. The liquid inside the liquid storage device 140 may be smoothly conveyed through the liquid conveying hole 301 to the liquid conveyer 206.

More specifically, a liquid storage cotton column may be provided at an inner side of the liquid conveying hole, and adapted to convey the liquid inside the liquid storage device 140 to the atomizer sleeve 207 for the convenience of liquid conveyance.

The second screw section 208 is provided at an end, connected to the liquid storage device 140, of the atomizer holder 201. The liquid storage device 140 is connected with the atomizer holder 201 in a removable manner through the second screw section. And the second screw section 208 and assemblies on the atomizer holder 201 may be replaced according to the user's requisition, which is convenient to maintain the electronic cigarette.

Further referring to FIG. 2, the first screw section 202 and the second screw section 208 may be thread sections with opposite turning directions.

For example, if the first screw section 202 is a leftward thread, the second screw section 208 is a rightward thread. Alternatively, if the first screw section 202 is a rightward thread, the second screw section 208 is a leftward thread.

Figure 3:
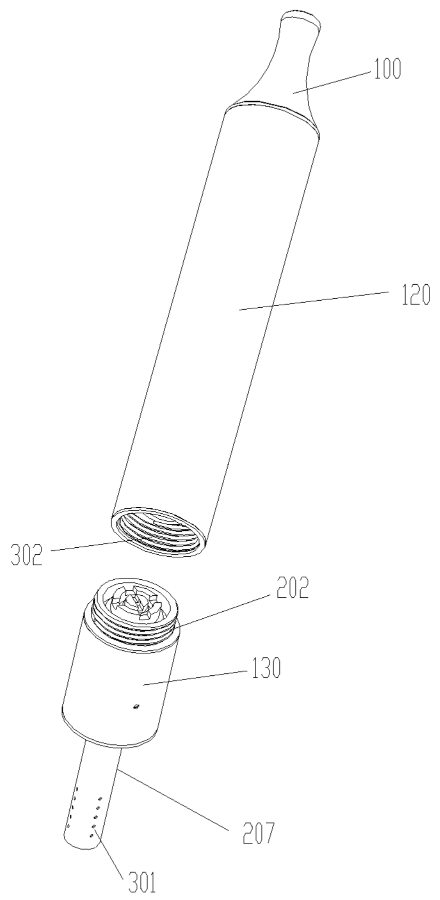
FIG. 3 is a partial exploded view of an electronic cigarette according to another preferable embodiment of the disclosure.

Further referring to FIG. 3, if the first screw section 202 is a thread section, a third screw section 302 of the battery rod assembly 120 is threads matching with the thread section of the first screw section 202.

The third screw section 302 of the battery rod assembly is connected with the first screw section 202 of the atomizing assembly 130 through threads.

Figure 4:
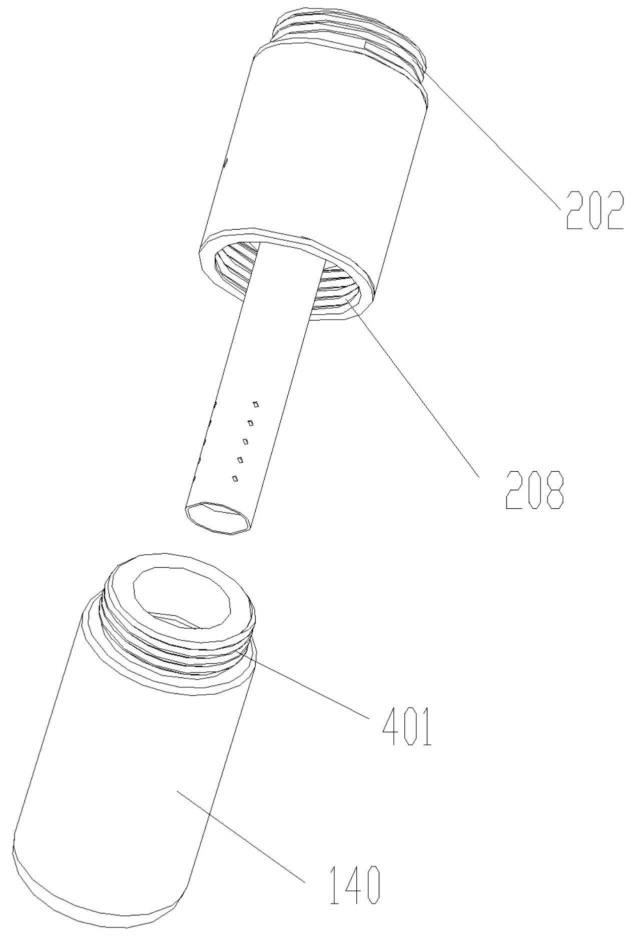
FIG. 4 is a partial exploded view of an electronic cigarette according to another preferable embodiment of the disclosure.

As shown in FIG. 4, if the second screw section 208 is a thread section, a fourth screw section 401 of the liquid storage device 140 is threads matching with the thread section of the second screw section 208.

The fourth screw section 401 of the liquid storage device 140 is connected with the second screw section 208 of the atomizing assembly 130 through threads.

Because the thread direction of the first screw section 202 is opposite to that of the second screw section 208, the thread direction of the third screw section 302 is opposite to that of the fourth screw section 401.

That is, the direction of the force to be exerted to remove the battery rod assembly is opposite to that of the force to be exerted to remove the liquid storage device 140. Therefore, when the user exerts a force in a certain direction upon an electronic cigarette, it will not happen that the liquid storage device 140 has already been loosely unscrewed from the atomizing assembly 130, and the battery rod assembly 120 has not yet been unscrewed and taken out; or it won't happen that the liquid storage device 140 has not yet been unscrewed, and the battery rod assembly has already been unscrewed. Thus, the mis-operation may hence be effectively avoided.

It shall be understood that, the connection of the first screw section 202 and the third screw section 302, and the connection of the second screw section 208 and the fourth screw section 401 will not be limited to threads with opposite directions.

Figure 5:
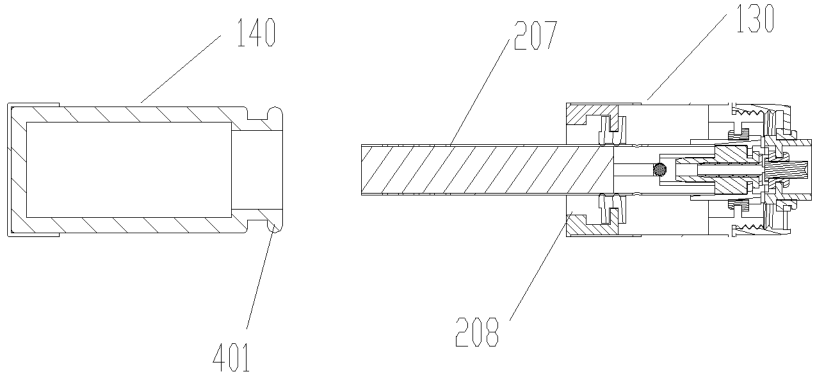
FIG. 5 is a partial sectional view of an electronic cigarette according to another preferable embodiment of the disclosure.

For example, as shown in FIG. 5, the fourth screw section 401 may also be configured as a swivel coupler section. The second screw section, matching with the fourth screw section 401, may be a clamping groove. The swivel coupler section may be provided inside the stuck groove.

The fourth screw section 401 may also be configured as a clamping groove, and the second screw section 208 configured as a swivel coupler section.

Alternatively, the first screw section 202 is a swivel coupler section, and the third screw section 302 is a clamping groove.

Alternatively, the first screw section 202 is a clamping groove, and the third screw section 302 is a swivel coupler section;

The specific configuration structure will not be limited in this embodiment, as long as the turning direction of the first screw section 202 is opposite to that of the second screw section 208.

In the disclosure, as shown in FIG. 1, the atomizing assembly 130 and the battery rod assembly 120 are coaxially arranged. The fume suction end 100 provided outside one end of the battery rod assembly 120 may be arranged coaxially with the battery rod assembly 120. This arrangement manner may make an appearance of the electronic cigarette imitate a real cigarette, and the overall shape of the fume passage is straight, which can effectively reduce liquid accumulation.

Alternatively, the fume suction end 100 may be provided at a middle portion of the battery rod assembly 120, or the fume suction end 100 may be provided at the portion of the battery rod assembly away from the atomizing assembly. This arrangement manner can effectively reduce liquid accumulation.

In the disclosure, the position of the fume suction end 100 will not be limited in this embodiment. In order that the overall structure of the electronic cigarette imitates a real cigarette and meets the user's smoking habits, the atomizing assembly 130 may be arranged coaxially with the battery rod assembly 120.

The detailed arrangement will not be limited in this embodiment. For example, the battery rod assembly 120, the atomizing assembly 130 and the liquid storage device 140, which are sequentially connected, may be staggered to form the electronic cigarette in an irregular shape. The irregular shape may be any shape.

The atomizing assembly 130 may also be arranged non-coaxially with the battery rod assembly 120. That is, the liquid storage device 140 is arranged parallel to the atomizing assembly 130, and both the liquid storage device 140 and the atomizing assembly 130 are connected with the battery rod assembly 120 to form the electronic cigarette in a T-shape.

The overall appearance of the electronic cigarette is not limited in this embodiment, as long as the liquid storage device 140 is provided at the place away from the fume suction end 100.

The structure of the battery rod assembly of the electronic cigarette according to the disclosure is illustrated in conjunction with the embodiment shown in FIG. 6 as follows:

The battery rod assembly includes: a battery sleeve 601; a battery 602; a battery holder 603; a battery electrode 604; and a fume passage 605.

The fume suction end 100 shown in FIG. 1 may be formed by extending an end of the battery sleeve 601 as integration; or connecting the suction nozzle as the fume suction end 100 with the battery sleeve 601 in a removable manner, the specific arrangement manner of which will not be limited in this embodiment.

In this embodiment, the fume suction end 100 connected in a removable manner may be replaced or cleaned by the user whenever necessary, which is convenient for the user to use.

The battery 602 is provided inside the battery sleeve 601.

The battery holder 603 is provided inside the battery sleeve 601 and adapted to fix the battery 602.

The battery electrode 604 is provided at one end of the battery holder 603 and connected with both the battery 602 and the atomizer electrode 203.

Figure 6:
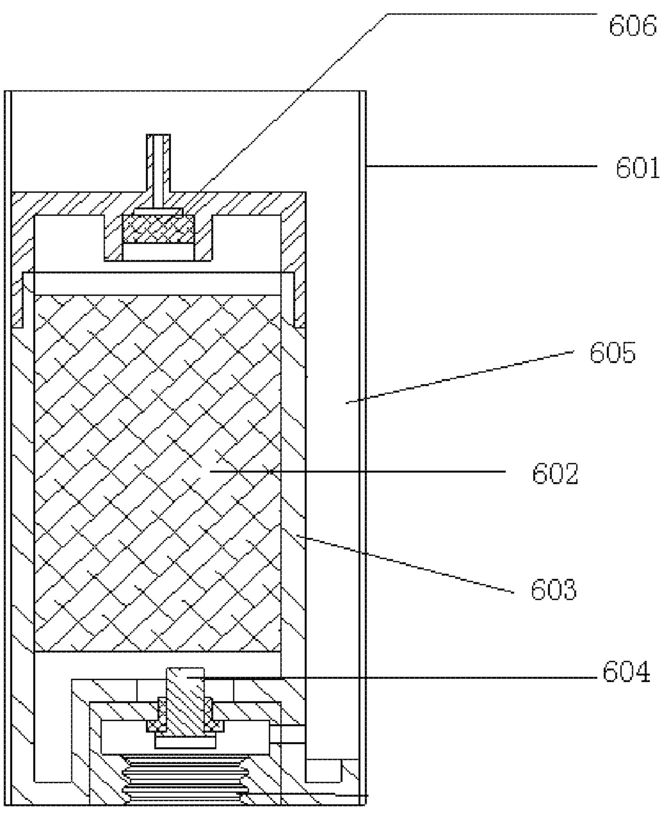
FIG. 6 is a sectional structural view of a battery rod assembly of an electronic cigarette according to another preferable embodiment of the disclosure.

Further referring to FIG. 6, the fume passage 605 is provided inside the battery rod assembly 120, and adapted to communicate with the fume suction end 100 and an air intake.

Preferably, the fume passage 605 is sealedly provided inside the battery rod assembly 120, i.e., separated from other electronic elements inside the battery rod assembly 120.

The air intake of the fume passage 605 may be arranged in two manners. It shall be understood that the below arrangement of the air intake is just for exemplary illustration, which will not be limited here, as long as the air intake of the body of the electronic cigarette is connected with the fume suction end 100 through the fume passage 605.

In the first arrangement, the air intake may be provided on a contact surface of the atomizing assembly 130 and the liquid storage device 140. Specially, a protruding block or a protruding ridge section be provided on the contact surface of the atomizing assembly 130 and the liquid storage device 140, to form the air intake, through which the air may be flowed into the fume passage, between the atomizing assembly 130 and the liquid storage device 140 connected through threads. The air may be flowed into the fume passage through the air intake.

It shall be understood that the arrangement manner of the air intake will not be limited, as long as the air intake may be formed between the atomizing assembly 130 and the liquid storage device 140, through which the air may be flowed into the fume passage.

Figure 7:
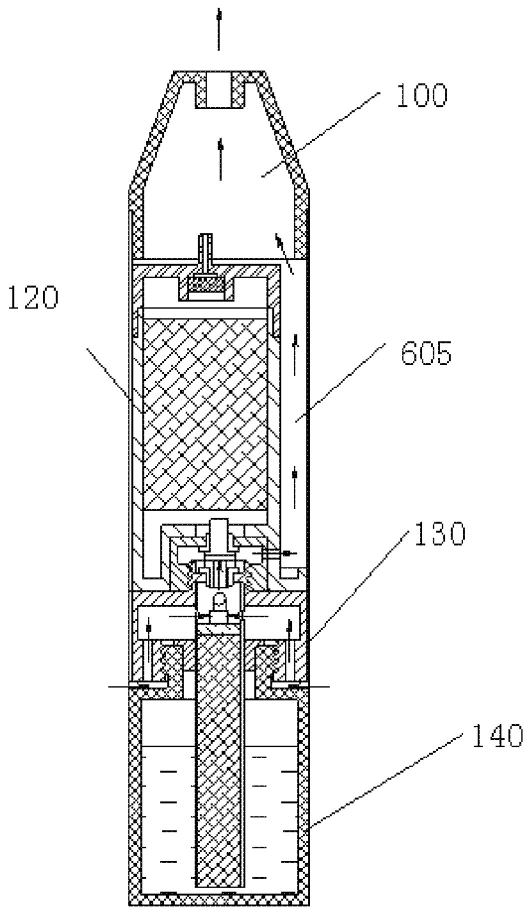
FIG. 7 is a sectional structural view of an electronic cigarette according to another preferable embodiment of the disclosure.

The fume suction end 100 and the air intake can be communicated through the fume passage 605. Referring to FIG. 7, a sectional view of the electronic cigarette is shown, where the air intake is provided on the contact surface of the atomizing assembly 130 and the liquid storage device 140.

As shown in FIG. 7, the air intake provided on the contact surface of the atomizing assembly 130 and the liquid storage device 140 is communicated with the fume suction end 100 through the fume passage 605.

In the embodiment, the direction of the air flow inside the electronic cigarette is shown by the arrow. As shown in FIG. 7, the air flow does not pass through the liquid storage device 140, resulting in that the liquid atomized by the atomizing assembly 130 may be flowed to the fume suction end 100 without passing through the liquid storage device 140, and thus the fumes will not be condensed due to the fume inhaling of the liquid storage device 140 and the fume passage 605 will not be blocked.

In the second arrangement manner, the air intake may also be provided on the outer surface of the atomizing assembly 130, the specific position and the amount of which will not be limited herein.

Figure 8:
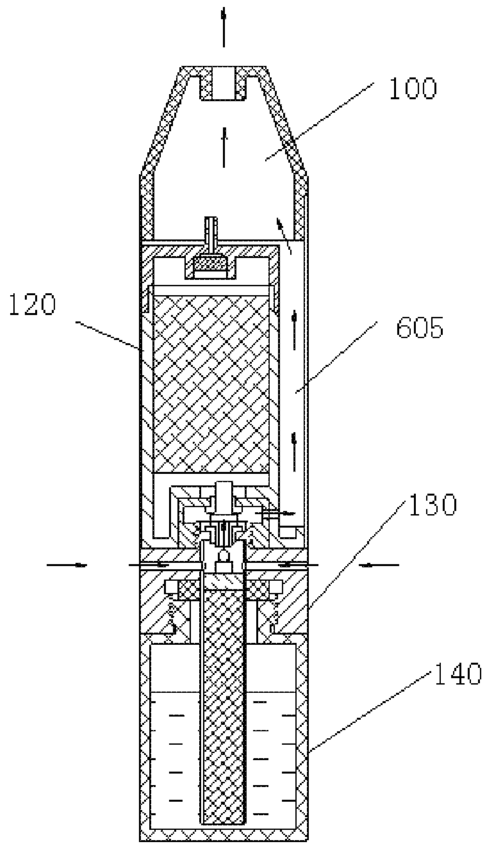
FIG. 8 is a sectional structural view of an electronic cigarette according to another preferable embodiment of the disclosure.

The fume suction end 100 and the air intake may be communicated through the fume passage 605. Referring to FIG. 8, a sectional schematic view of the electronic cigarette is shown, where the air intake is provided on the outer surface of the atomizing assembly 130.

As shown in FIG. 8, the air intake provided on the outer surface of the atomizing assembly 130 is communicated with the fume suction end 100 through the fume passage 605.

Specifically, in the embodiment, the direction of the air flow inside the electronic cigarette is shown by the arrow. As shown in FIG. 8, the air flow does not pass through the liquid storage device 140, resulting in that the liquid atomized by the atomizing assembly 130 may be flowed to the fume suction end 100 without passing through the liquid storage device 140, and the fumes will not be condensed due to the fume inhaling of the liquid storage device 140, and therefore the fume passage 605 will not be blocked.

Furthermore, there may be two types of control modes for atomizing the liquid by the battery rod assembly 120 according to the disclosure.

In the first mode, referring to FIG. 6, an air flow sensor 606 is provided inside the battery sleeve 601 near the fume suction end 100, and adapted to generate a pulse signal.

The air flow sensor 606 may generate a pulse signal when it is detected that the air pressure in the fume passage 605 is reduced, i.e., when a user smokes.

In this embodiment, since the air flow sensor 606 is close to the fume suction end 100, the sensitivity for the air flow sensor to sense a user's smoking behaviors is improved, and the user may more effectively use the electronic cigarette.

A micro controller is connected with both the air flow sensor 606 and the battery 602, and adapted to generate a control signal according to the pulse signal. The micro controller is further connected to the electric heating wire assembly 205, and the electric heating wire assembly 205 may atomize the liquid according to the control signal.

With this arrangement manner, the smoking may imitate the smoking effect of a real cigarette, and the user may such the atomized liquid through the fume suction end 100.

Figure 9:
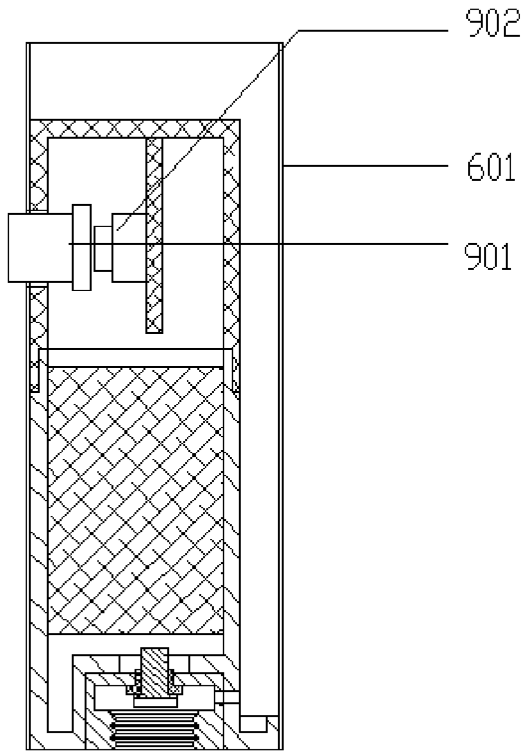
FIG. 9 is another sectional structural view of a battery rod assembly of an electronic cigarette according to a preferable embodiment of the disclosure.

Reference may be made to FIG. 9 for the second control mode.

A button 901 is provided on the battery sleeve 601, and adapted to receive a user's operation instruction.

A micro touch switch 902 is connected to the button 901 and adapted to generate a control signal according to the operation instruction.

The micro touch switch 902 is also connected with the electric heating wire assembly 205, and the electric heating wire assembly 205 may atomize the liquid according to the control signal.

With this arrangement manner, the user may smoke the electronic cigarette without the fume suction end 100, and the liquid may be atomized by the electric heating wire assembly of the electronic cigarette solely by pressing the button 601.

Figure 10:
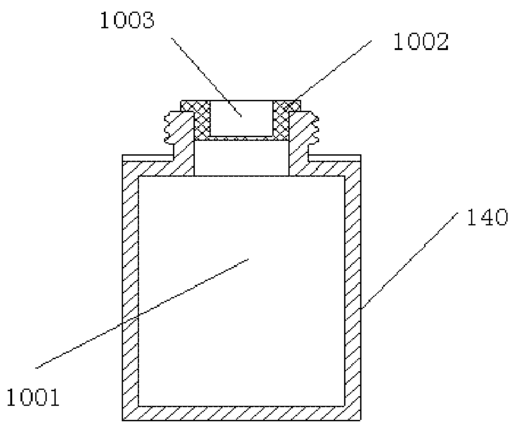
FIG. 10 is another sectional structural view of a liquid storage device of an electronic cigarette according to a preferable embodiment of the disclosure.

The specific structure of the liquid storage device provided in the disclosure is illustrated in conjunction with an embodiment shown in FIG. 10 as follows:

As shown in FIG. 10, a sealed chamber 1001 is provided inside the liquid storage device 140, and adapted to store the liquid is stored.

In order to let the user know the amount of the remaining liquid in the liquid storage device 140, the liquid storage device 140 is a transparent container. In this way, the user may know the amount of the remaining liquid in the liquid storage device 140 through the transparent liquid storage device 140 whenever necessary, which is convenient for the user to replace the liquid storage device 140 in time.

Preferably, the liquid storage device 140 is a glass bottle. Because the glass has stable chemical properties, the flavor of the cigarette may not easily be influenced by some chemical reactions.

More preferably, scales are provided at a surrounding wall of the liquid storage device 140 which is made of glasses, allowing the user to estimate the time that the remaining liquid can be used, which is convenient for the user to use. In order to imitate a real cigarette, the length of the electronic cigarette is generally equal to the real cigarette. Also, in order to reduce the charging frequency and increase the service life of the battery rod assembly 120, the length of the battery rod assembly 120 may occupy at least half of the overall length of the electronic cigarette. When the user smokes the electronic cigarette according to the embodiment, he or she may naturally hold the upper portion of the electronic cigarette near to the fume suction end 100. In this embodiment, the liquid storage device 140 is arrange at the end away from the fume suction end 100, and thus the holding forces exerted upon the liquid storage device by the user are uniform, and the liquid storage device 140 under even forces may evenly output the amount of liquid to the atomizing assembly 130. In this way, the output stability of the fumes may be effectively guaranteed, and it is avoided that in the existing technology, the liquid is evenly provided due to different forces exerted upon the end of the atomizer, resulting in an uneven amount of fumes.

Preferably, a protective cartridge (not shown in Figures) is provided on the liquid storage device 202 to avoid the situation that the liquid storage device 202 made of glasses may be fallen and broken.

More preferably, the protective cartridge is provided with a liquid watching window adapted to watch the liquid by the user.

In order to effectively maintain a good sealing quality of the liquid storage device 140 to effectively avoid liquid leakage, two arrangement manners may be adopted in this embodiment;

In the first arrangement manner, as shown in FIG. 2, in order that the liquid storage device 140 connected to the atomizing assembly 130 possess a good sealing quality, and that the liquid inside the liquid storage device 140 won't be leaked out, a sealing ring 209 adapted to seal the liquid storage device 140 is provided at a joint of the atomizer holder 201 and the liquid storage device 140.

The sealing ring provided on the atomizer holder 201 may effectively maintain the sealing quality of the liquid storage device 140.

In the second arrangement manner, as shown in FIG. 10, an annular sealing plug 1002 with a through hole is sealedly provided at the mouth of the liquid storage device 140.

A pierceable film 1003 is provided inside the through hole of the annular sealing plug 1002 and adapted to seal the liquid storage device 140.

When the atomizer sleeve 207 is inserted inside the sealed chamber 1001 of the liquid storage device 140, the atomizing sleeve 207 pierces the pierceable film 1003. With the pierceable film, the liquid storage device 140 inserted into the atomizer sleeve 207 maintains a good sealing quality, which therefore effectively avoids the liquid leakage.

Since the liquid storage device 140 according to this embodiment is provided with an annular sealing cork 1002 with the pierceable film 1003, the liquid storage device 140 maintains a good sealing quality, which therefore effectively avoids the liquid leakage, prolongs the service time of the electronic cigarette, and guarantees the service life of the electronic cigarette.

Figure 11:
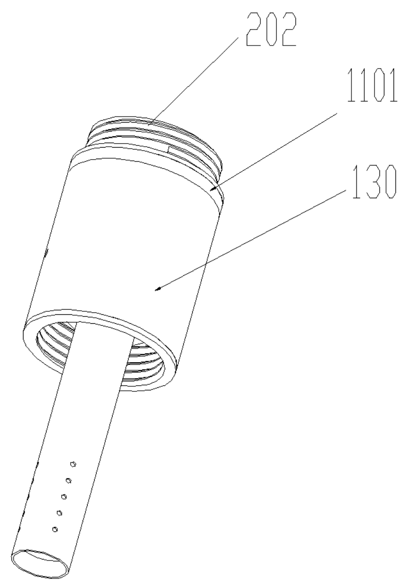
FIG. 11 is another structural view of an atomizing assembly of an electronic cigarette according to a preferable embodiment of the disclosure.

Referring to FIG. 11, a sealing ring 1101 is provided at a joint of the first screw section 202 of the atomizing assembly 130 and the third screw section 302 of the battery rod assembly 120. The sealing ring 1101 effectively guarantees the concentration of the atomized liquid inside the electronic cigarette.

Figure 12:
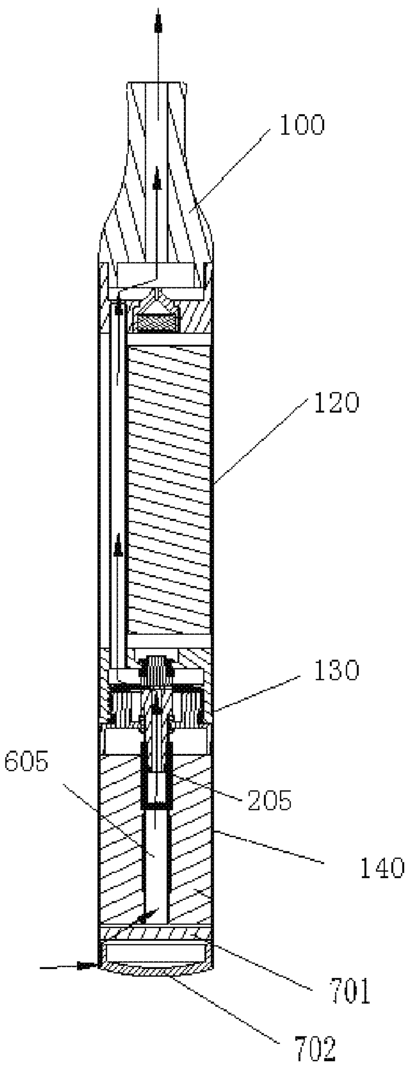
FIG. 12 is a sectional structural view of an electronic cigarette according to another preferable embodiment of the disclosure.

The electronic cigarette according to an embodiment of the disclosure may also imitate, in the aspect of the light effect, the smoking effect of a real cigarette. A specific structure is shown in FIG. 12, and the electronic cigarette includes the followings.

A fume suction end 100 and a battery rod assembly 120 are provided. The specific structure of the fume suction end

100 and the battery rod assembly 120 may be referred to in the previous embodiments, which will be omitted in this embodiment.

In this embodiment, the liquid storage device 140 and the atomizing assembly 130 are arranged as integration, and the liquid storage device 140 is provided at one end of the body of the electronic cigarette away from the fume suction end 100.

Preferably, a fume passage 605 is provided inside the liquid storage device 140. An air intake communicated with the fume passage 605 is provided at the bottom of the liquid storage device 140. The fume passage 605 is extended to and communicated with the fume suction end 100.

The direction of the air flow is shown by the arrow in FIG. 12. As shown in FIG. 12, compared with the previous embodiment, the fume passage in this embodiment is longer. The longer fume passage 605 may lower the temperature of the liquid atomized by the electric heating wire assembly, which guarantees the user experience of the smoking process.

More preferably, a lamp module 701 may be provided at the bottom of the body of the electronic cigarette. When a user smokes through the fume suction end 100, the lamp module 701 may emit lights, and the lights may imitate the burning effect of tobaccos. Different lighting effects may be provided according to the user's needs.

An end cover 702 is provided at the bottom of the body of the electronic cigarette and adapted to contain the lamp module 701. The end cover 702 is a transparent or a non-transparent casing.

In order that the liquid inside the liquid storage device may be conveyed more smoothly to the liquid conveyor, another structure of the electronic cigarette is illustrated in conjunction with the embodiment shown in FIG. 13 as follows.

The electronic cigarette includes a fume suction end 100 and a battery rod assembly 120. The specific structures of the fume suction end 100 and the battery rod assembly 120 may be referred to in the previous embodiment, which will be omitted in this embodiment.

In this embodiment, the liquid storage device 140 adapted to store the liquid is provided on an outer wall of the atomizing assembly 130. The liquid inside the liquid storage device 140 may be conveyed through the liquid conveying holes on the atomizing sleeve 207 to the liquid conveyer 206 inside the atomizing sleeve 207, to atomize the liquid by the electric heating wire assembly 205. The specific structure inside the atomizing assembly 130 may be referred to in the previous embodiment, which will not be limited in this embodiment.

In this embodiment, the flow direction of the liquid inside the liquid storage device 140 is vertical to or have an angle with the flow direction of the liquid in the atomizing sleeve 207 conveyed to the electric heating wire assembly for atomization, so that an excessive conveyance of the liquid to the atomizer due to a shake or the like may be avoided. In this way, the liquid in the liquid storage device may be stably conveyed to the liquid conveyer in the atomizing sleeve, which ensures an even amount of fumes. Besides, with this structure a breakage of the liquid storage device made of a glass material may also be avoided when the electronic cigarette falling off with the end hitting the ground.

In this embodiment, the liquid storage device 140 is connected to the atomizing assembly 130 through threads, or in other manners such as a coupler. The specific connection manner is not limited in this embodiment.

It shall be understood that the amount and the position of the liquid storage device 140 provided on the side wall of the atomizing assembly 130 is not limited in this embodiment.

Figure 13:
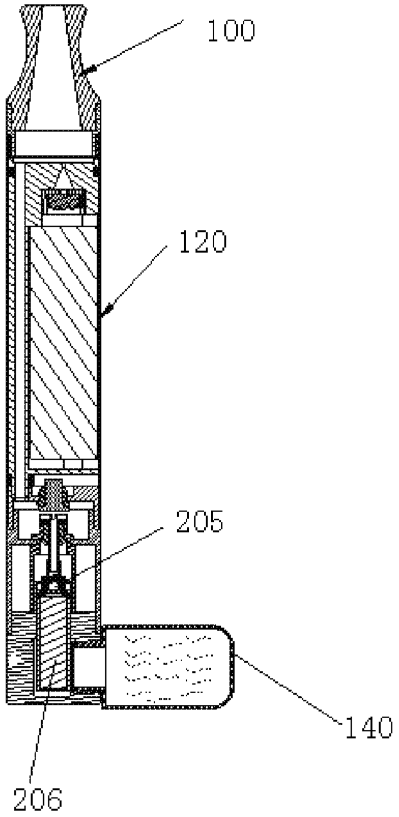
FIG. 13 is a sectional structural view of an electronic cigarette according to another preferable embodiment of the disclosure.

As shown in FIG. 13, when the amount of the liquid storage device 140 provided on the side wall of the atomizing assembly 130 is one, the body of the electronic cigarette represents an L-shape.

Figure 14:
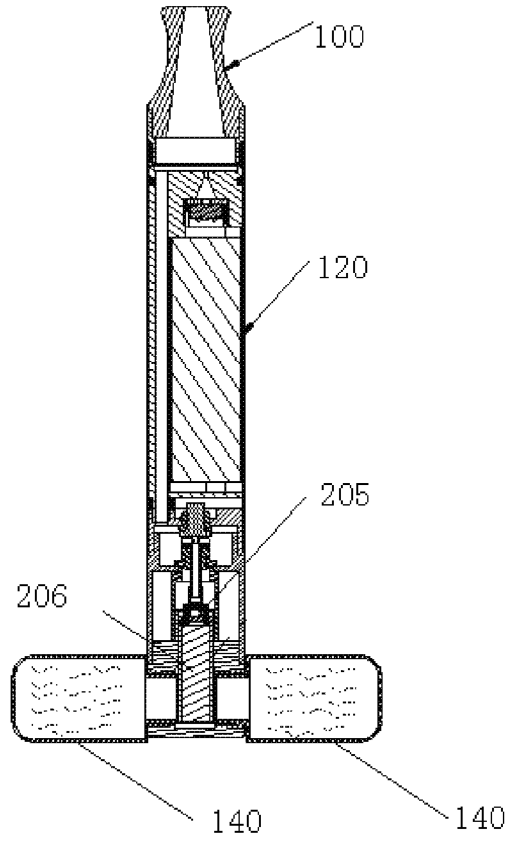
FIG. 14 is a sectional structural view of an electronic cigarette according to another preferable embodiment of the disclosure.

Alternatively, as shown in FIG. 14, when two liquid storage devices 140 are provided on the side wall of the atomizing assembly 130 and are arranged oppositely, the body of the electronic cigarette represents a T-shape.

The technical solution according to the embodiments of the disclosure will be described clearly and fully in conjunction with the appended drawings. Apparently, the described embodiments are not the whole but just part of the embodiments of the present invention. All the other embodiments that can be obtained by those with ordinary skills in the art without creative work shall fall into the scope of protection sought for in the present invention.

The embodiments of the present invention are described herein in a progressive manner, each of which emphasizes the differences from others; hence for the same or similar parts between the embodiments, one can refer to the other embodiments.

The above description of the disclosed embodiments enables those skilled in the art to implement or use the invention. Numerous modifications to the embodiments will be apparent to those skilled in the art, and the general principle herein can be implemented in other embodiments without departing from the spirit or scope of the invention. Therefore, the present invention shall not be limited to the embodiments described herein, but shall cover the widest scope consistent with the principle and novelty features disclosed herein.

The invention claimed is:

1. An electronic cigarette, comprising:

an atomizing assembly adapted to atomize liquid, a battery rod assembly adapted to supply power to the atomizing assembly, and a liquid storage device adapted to store the liquid;

wherein a first screw section and a second screw section are respectively provided at two ends of the atomizing assembly, and a turning direction of the first screw section is opposite to a turning direction of the second screw section;

a fume suction end and a third screw section matched with the first screw section are respectively provided at two ends of the battery rod assembly; and a fourth screw section matched with the second screw section is provided at an open end of the liquid storage device; and wherein the liquid storage device is provided at an end of a body of the electronic cigarette away from the fume suction end.

2. The electronic cigarette according to claim 1, wherein each of the screw sections is a thread section or a swivel coupler section.

3. The electronic cigarette according to claim 2, wherein the atomizing assembly and the battery rod assembly are coaxially arranged.

4. The electronic cigarette according to claim 2, wherein the atomizing assembly further comprises:

an atomizer holder;

an atomizer electrode fixed inside the first screw section and electronically connected with an electric heating wire assembly;

an insulating ring provided between the first screw section and the atomizer electrode; and an atomizer sleeve provided on the atomizer holder, wherein the liquid conveyer is provided inside the atomizer sleeve.

5. The electronic cigarette according to claim 2, wherein, the battery rod assembly comprises:

a battery sleeve;

a battery contained in the battery sleeve;

a battery holder provided inside the battery sleeve and adapted to fix the battery; and a battery electrode provided at an end of the battery holder and connected with the battery and an atomizer electrode.

6. The electronic cigarette according to claim 2, wherein the liquid storage device is a transparent container with scales.

7. The electronic cigarette according to claim 2, wherein a fume passage adapted to communicate the fume suction end with an air intake is provided inside the battery rod assembly;

the air intake is provided on a contact surface of the atomizing assembly and the liquid storage device; or the air intake is provided on an outer wall of the atomizing assembly.

8. The electronic cigarette according to claim 1, wherein the atomizing assembly and the battery rod assembly are coaxially arranged.

9. The electronic cigarette according to claim 8, wherein the atomizing assembly comprises:

an electric heating wire assembly adapted to atomize the liquid; and a liquid conveyer adapted to convey the liquid in the liquid storage device to the electric heating wire assembly for atomization.

10. The electronic cigarette according to claim 1, wherein the atomizing assembly further comprises:

an atomizer holder;

an atomizer electrode fixed inside the first screw section and electronically connected with an electric heating wire assembly;

an insulating ring provided between the first screw section and the atomizer electrode; and an atomizer sleeve provided on the atomizer holder, wherein a liquid conveyer is provided inside the atomizer sleeve.

11. The electronic cigarette according to claim 10, wherein a plurality of liquid conveying holes are provided on a side wall of the atomizing sleeve; and a liquid storage cotton column is provided at an inner side of the liquid conveying holes and adapted to convey the liquid in the liquid storage device to the atomizing sleeve.

12. The electronic cigarette according to claim 10, wherein a sealing ring adapted to seal the liquid storage device is provided at a joint of the atomizer holder and the liquid storage device.

13. The electronic cigarette according to claim 1, wherein, the battery rod assembly comprises:

a battery sleeve;

a battery contained in the battery sleeve;

a battery holder provided inside the battery sleeve and adapted to fix the battery; and a battery electrode provided at an end of the battery holder and connected with the battery and an atomizer electrode.

14. The electronic cigarette according to claim 13, wherein a suction nozzle, provided as a fume suction end, is connected with the battery sleeve in a removable manner.

15. The electronic cigarette according to claim 13, wherein an annular sealing plug with a through hole is sealingly engaged with the open end of the liquid storage device; and a pierceable film is provided inside a liquid conveying hole of the annular sealing plug and adapted to seal the through hole.

16. The electronic cigarette according to claim 1, wherein the liquid storage device is a transparent container with scales.

17. The electronic cigarette according to claim 16, wherein the liquid storage device is a glass bottle with scales.

18. The electronic cigarette according to claim 1, wherein a sealing ring is provided at a joint of the first screw section of the atomizing assembly and the third screw section of the battery rod assembly.

19. The electronic cigarette according to claim 1, wherein a fume passage adapted to communicate the fume suction end with an air intake is provided inside the battery rod assembly;

the air intake is provided on a contact surface of the atomizing assembly and the liquid storage device; or the air intake is provided on an outer wall of the atomizing assembly.

* * * * *